US012405335B2

(12) United States Patent
Barberi et al.

(10) Patent No.: US 12,405,335 B2
(45) Date of Patent: Sep. 2, 2025

(54) DAILY MRgRT QA PHANTOM

(71) Applicant: MODUS MEDICAL DEVICES INC., London (CA)

(72) Inventors: Enzo Antonio Barberi, London (CA); David John Munro Miller, London (CA)

(73) Assignee: MODUS MEDICAL DEVICES INC., London (CA)

( * ) Notice: Subject to any disclaimer, the term of this patent is extended or adjusted under 35 U.S.C. 154(b) by 0 days.

(21) Appl. No.: 16/857,579

(22) Filed: Apr. 24, 2020

(65) Prior Publication Data

US 2020/0341104 A1  Oct. 29, 2020

Related U.S. Application Data

(60) Provisional application No. 62/839,237, filed on Apr. 26, 2019.

(51) Int. Cl.
*G01R 33/58* (2006.01)
*A61B 5/055* (2006.01)
*G01R 33/36* (2006.01)

(52) U.S. Cl.
CPC ........... *G01R 33/58* (2013.01); *A61B 5/055* (2013.01); *G01R 33/3671* (2013.01)

(58) Field of Classification Search
CPC ...... G01R 33/58; G01R 33/3671; A61B 5/055
See application file for complete search history.

(56) References Cited

U.S. PATENT DOCUMENTS

| | | | | |
|---|---|---|---|---|
| 4,888,555 | A * | 12/1989 | Vaughan ............... | G01R 33/58 324/318 |
| 7,038,451 | B2 * | 5/2006 | Speckner ............... | G01R 33/58 324/307 |
| 7,699,522 | B2 * | 4/2010 | Varchena ............ | A61N 5/1049 378/207 |
| 8,666,133 | B2 * | 3/2014 | Vermandel ............ | G01R 33/58 378/207 |
| 8,814,572 | B2 * | 8/2014 | Eberler ................. | G01R 33/58 434/267 |
| 9,865,180 | B2 * | 1/2018 | Saloux ................. | G09B 23/286 |
| 9,880,251 | B2 * | 1/2018 | Kerins ............... | G01R 33/4806 |
| 10,180,484 | B2 * | 1/2019 | Barberi ................. | G01R 33/58 |
| 10,492,755 | B2 * | 12/2019 | Lin ....................... | A61B 6/461 |
| 10,607,099 | B2 * | 3/2020 | Cai ........................ | G06T 7/66 |
| 2003/0122544 | A1 * | 7/2003 | Parker ................... | A61B 6/583 324/309 |
| 2005/0134264 | A1 * | 6/2005 | Speckner ............... | G01R 33/58 324/307 |
| 2007/0287904 | A1 * | 12/2007 | Li ......................... | A61B 5/055 600/410 |

(Continued)

*Primary Examiner* — Dixomara Vargas

(57) ABSTRACT

A MRI quality assurance phantom with a base and a vertical body mounted on the base. At lease one of the base and the vertical body have a housing made of a MRI invisible material and enclose a sealed reservoir filed with a MRI signal producing material. The vertical body has a generally planar face with one or more attachment points thereon for attachment of one or more accessories to the face of the vertical body. The interior walls of the housing, defining the shape of the sealed reservoir, have one or more defined structures formed thereon, suitable for image quality testing.

22 Claims, 9 Drawing Sheets

(56) References Cited

U.S. PATENT DOCUMENTS

| | | | | |
|---|---|---|---|---|
| 2008/0317198 | A1* | 12/2008 | Thornton | A61B 6/583 378/18 |
| 2009/0177075 | A1* | 7/2009 | Derakhshan | G01R 33/5614 600/410 |
| 2009/0225957 | A1* | 9/2009 | Varchena | A61N 5/1049 378/207 |
| 2012/0040322 | A1* | 2/2012 | Eberler | G01R 33/58 434/267 |
| 2013/0180556 | A1* | 7/2013 | Boyer | A47L 15/4253 312/351.3 |
| 2013/0200900 | A1* | 8/2013 | Buurman | G01R 33/50 324/318 |
| 2014/0266198 | A1* | 9/2014 | Tadic | G01R 33/56572 324/309 |
| 2016/0133159 | A1* | 5/2016 | Saloux | G09B 23/288 73/866.4 |
| 2017/0184696 | A1* | 6/2017 | Zuccolotto | G01R 33/31 |
| 2017/0192076 | A1* | 7/2017 | Kerins | G01R 33/58 |
| 2017/0205488 | A1* | 7/2017 | Barberi | G01R 33/58 |
| 2018/0014809 | A1* | 1/2018 | Lin | A61B 6/461 |
| 2018/0047303 | A1* | 2/2018 | Groenewald | A61B 6/583 |
| 2018/0113186 | A1* | 4/2018 | Kerins | G01R 33/4806 |
| 2018/0275240 | A1* | 9/2018 | Kim | G01R 33/58 |
| 2019/0054322 | A1* | 2/2019 | Yang | A61N 5/1081 |
| 2019/0113591 | A1* | 4/2019 | Barberi | G01R 33/58 |
| 2020/0061391 | A1* | 2/2020 | Krishnaswamy | A61N 5/1067 |
| 2020/0359988 | A1* | 11/2020 | Woods | A61B 6/08 |

\* cited by examiner

DAILY MRgRT QA PHANTOM

FIELD OF THE INVENTION

The present invention relates generally to a MRI quality assurance (QA) phantom apparatus. More specifically, the present invention relates to a magnetic resonance guided radiation therapy (MRgRT) QA phantom for daily use.

BACKGROUND OF THE INVENTION

Magnetic resonance imaging (MRI) is a well-established diagnostic imaging modality that is the gold standard for many clinically relevant diagnostic applications due to superior soft tissue contrast and the wide variety of contrast mechanisms that can reveal both subtle and dramatic anatomical, functional, and pathological details with higher sensitivity and specificity than other imaging modalities.

More recently, the advantages of MRI are being used in image guided applications such as neurosurgical planning and radiation planning and therapy. For example, in image guided radiation therapy, the ability to visualize active tumors and real-time radiation dose distributions is expected to result in higher targeted dose to tumor regions with a concomitant decrease in radiation exposure to healthy tissue, resulting in more efficient treatments and higher survival rates in afflicted patients. In some cases, image guided radiation therapy is the only viable treatment for certain types of cancer. Tools for MRI quality assurance (QA) have been available for diagnostic applications, and are limited to small fields of view (FOV) typically under 20 cm. MRI guided applications such as MR simulation, planning, and radiation therapy treatment involve the use of imaging large FOVs that can exceed 35 cm. An important unmet need related to magnetic resonance imaging guided simulation, planning, and radiation therapy daily QA over large FOVs therefore exists.

The recent introduction of MR guided Linac systems into the clinical radiation therapy setting has presented a paradigm shift in the treatment of cancer, with the exquisite soft tissue contrast only available through MR Imaging. The ability to clearly visualize tumors and organs at risk in real time and while moving will provide clinicians with the ability to reduce treatment margins, increase dose to the tumor, and decrease dose to healthy tissue. It is envisioned that current techniques will be expanded to include real time motion tracking with MR imaging with the ability to change or adapt the radiation beam to move with and precisely target moving tumors, eliminating the need to gate the radiation beam or require patients to employ breath hold techniques to localize the tumor. The result will be more effective treatment of cancers associated with high mortality due to their proximity to other sensitive or moving organs, such as pancreatic, liver, and lung cancer.

The ability to precisely target tumors with MR guided simulation, planning, and radiation treatment is entirely dependent on MR image quality. The development and implementation of next generation image quality assurance tools over large FOVs appropriate for these applications is required. The present invention relates to the design of a large field of view MR guided radiation therapy daily QA tool that is capable of generating a sufficiently broad amount of QA data in a rapid and quick fashion, as required for a daily QA tool, meeting the needs of clinicians for workflow efficiency.

SUMMARY OF THE INVENTION

A MRI quality assurance phantom, according to the present invention, has a base and a vertical body mounted on the base. At least one of the base and the vertical body have a housing made of a MRI invisible material and enclose a sealed reservoir filed with a MRI signal producing material. The vertical body has a generally planar face with one or more attachment points thereon for attachment of one or more accessories to the face of the vertical body.

In another embodiment, the housing has interior walls defining the shape of the sealed reservoir and having one or more defined structures formed thereon, suitable for image quality testing.

In another embodiment, the one or more defined structures includes a plurality of grooves arranged to form a grid. The defined structures may also or instead include modulation transfer function resolution structures or slice thickness ramps.

In another embodiment, the one or more defined structures are located within a plurality of image quality zones spaced apart within the plane of the sealed reservoir.

BRIEF DESCRIPTION OF THE DRAWINGS

The present invention will be further understood and supported using the following drawings and their associated descriptions. These descriptions and drawings are not meant to limit the invention by any circumstance and are to be interpreted as possible embodiments of the invention disclosed herein, in which.

DESCRIPTION OF THE INVENTION

Figure 1:
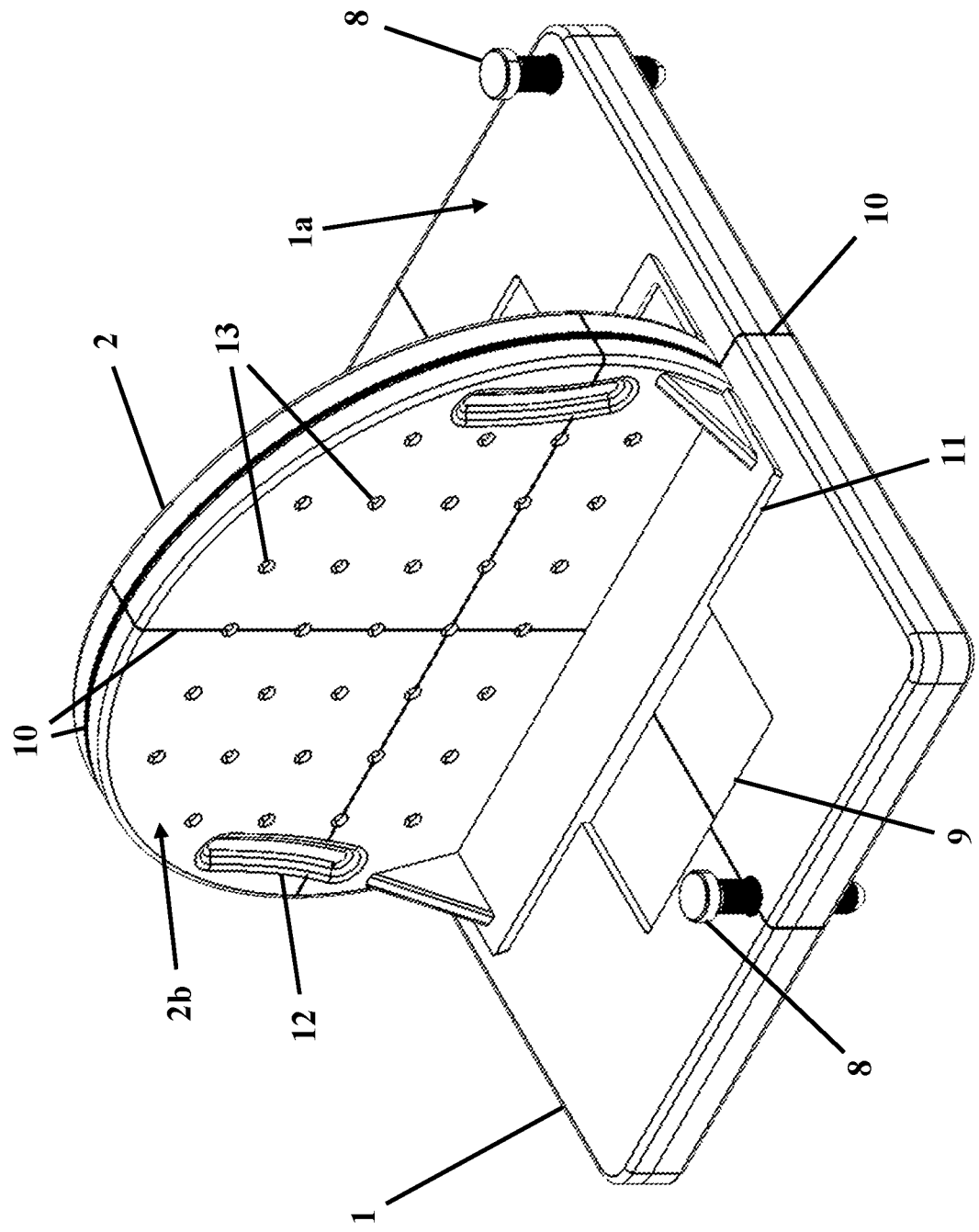
FIG. 1 is a perspective view of a daily MRgRT QA phantom, according to the present invention.

A daily MRgRT QA phantom, according to the present invention, is a combination of two closed acrylic housings, or shells, filled with MRI signal producing material (water, mineral oil, silicone oil or gels that produce an MRI signal), each with internal structures that can be used to measure MR image quality parameters quickly and easily, so as to facilitate daily QA testing with one or more of the following parameters, features, and capabilities:

- Scan time of 5 minutes or less;
- Horizontal structure to permit coronal plane image QA;
- Vertical structure to permit axial and sagittal plane image QA;
- Ability to rotate 2D vertical phantom from axial to sagittal plane;
- Adjustability to position phantom isocentre at standardized (i.e. DICOM™) isocentre on various MR and MR Linac systems;
- Alignment of megavolt (MV) treatment field with MRL and MR SIM isocentre and CT SIM isocentre with user selected multi-modality imaging target;
- One or more 2D grid planes within phantom for distortion visualization;
- Flood-field uniform plane for B0 assessment, uniformity, SNR (RF coil faults), and ghosting;
- User-selected positioning for offset landmarking;
- Couch shifts within OEM limits;
- QA per task group recommendations;
- Ferrous contamination detection;
- Daily dosimetry testing with ion chamber (or with film) for MR Linac systems;
- External laser alignment verification;
- Laser/MR isocentre offset constancy with user selected offset target;
- Low contrast object detectability;
- Slice thickness measurement;
- Spatial resolution verification;
- Phantom possesses a high bore fill factor (40 cm diameter range for MRgRT systems and large field of view of 35 cm for radiation therapy treatment volumes);
- Lightweight phantom (preferably <10 kg per section) with integrated handles;
- Pressure and temperature compensated MRI contrast media chambers;
- Level indicators and levelling platform with adjustable feet to permit positioning phantom at isocentre;
- Horizontal phantom base with contrast media to measure coil SNR in coronal plane that covers (typical) 500 mm long RF coil spine array FOV, with image QA structures; and
- Dosimetry measurement capabilities at user selected positions.

A Daily MRgRT QA phantom, according to the present invention, suitable for rapid daily QA as well as less frequent, time consuming dosimetry and image QA, is shown in FIGS. 1-7. The phantom has a horizontal base 1 and a vertical body 2 mounted on the base 1. At least one, but preferably both, of the base 1 and the vertical body 2 are made up of a housing made of a rigid MRI invisible material, containing one or more sealed reservoirs 3 containing a fluid MRI signal producing material. Preferably, the housing is made of acrylic, as it is closely susceptibility matched to human tissue, and the MRI signal producing material is an MRI contrast medium, such as mineral oil with a close susceptibility match to human tissue. Alternatively, the housing may be another human tissue susceptibility matched plastic and the MRI contrast media may be water, silicone oil, or a gel that produces an MRI signal. Mineral oil is preferred for use in the phantom, since it is intended for use in a wide range of applications, including radiation dosimetry testing. Unlike some other common MRI contrast media, mineral oil is both physiologically relevant, having a density similar to that of adipose tissue, and is stable under repeated radiation dosing.

Figure 12:
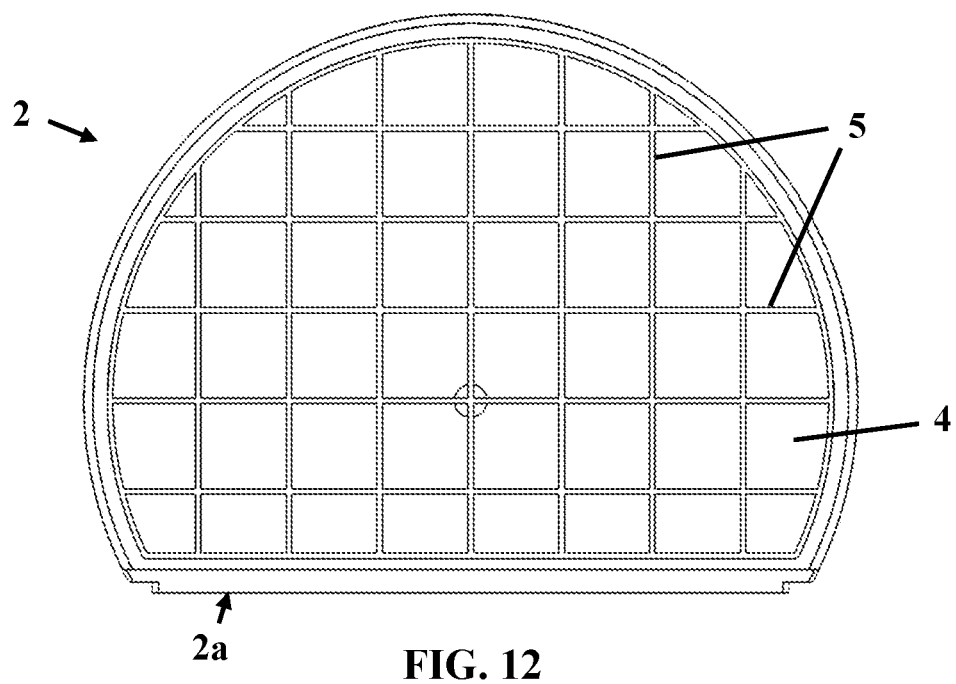
FIG. 12 is a rear cutaway view of the vertical body of the phantom, with the rear face removed to show internal features of the front face of the vertical body.
Figure 13:
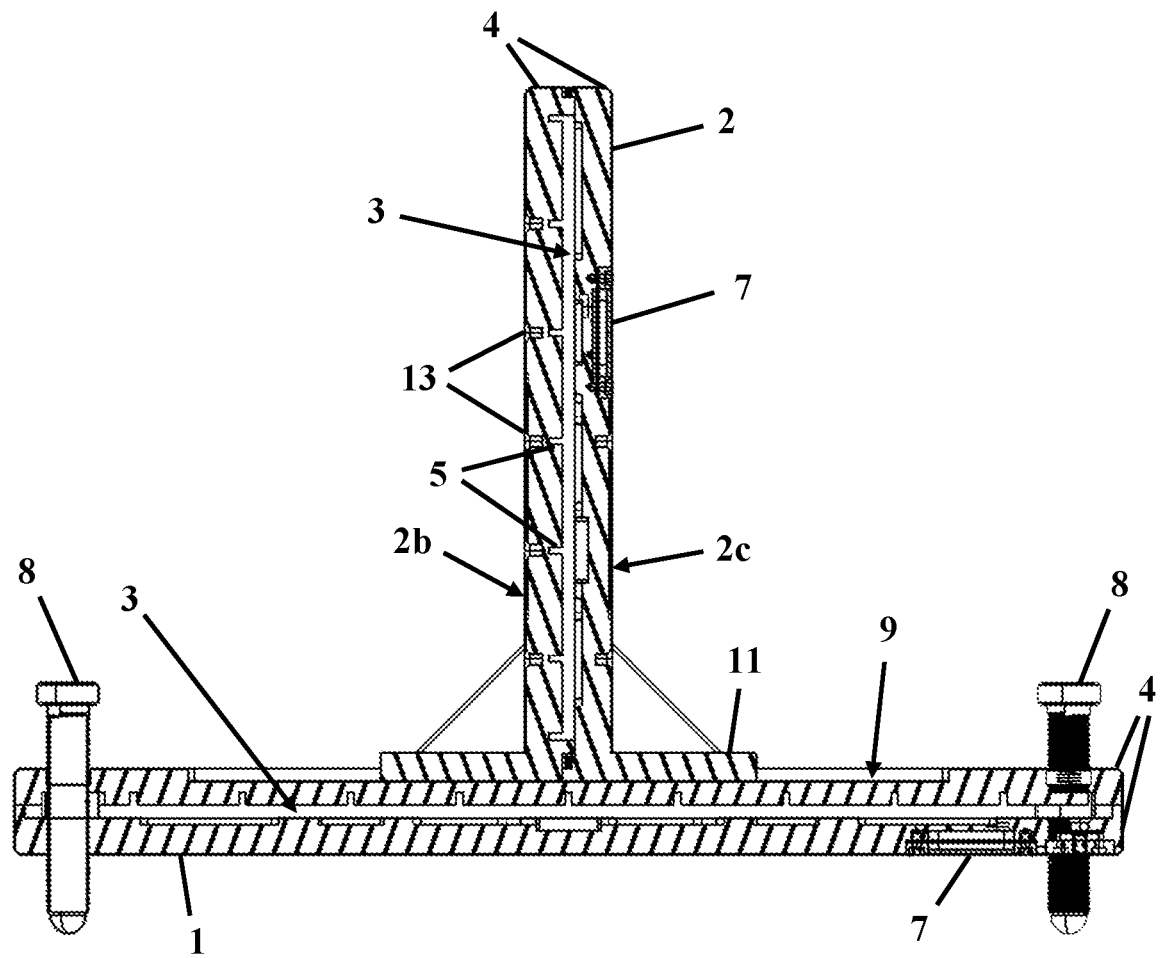
FIG. 13 is a side cross-sectional view of the phantom, along the lines A-A shown in FIG. 6, with certain internal features removed to more clearly show the internal reservoirs.

As shown in FIG. 13, the housing of either or both of the base 1 and the vertical body 2 is made up of two opposing sheets 4, which are separated by a defined distance and sealed about their perimeter edges to define a sealed reservoir 3 therebetween having defined dimensions. Preferably, the two opposing sheets 4 are separated by a distance of 6 mm, but other dimensions may be used depending on the application. One or both of the interior faces of the opposing sheets 4 may have a pattern of structures formed thereon. Preferably, one of the opposing sheets has a plurality of grooves 5 formed at regular intervals defining a grid thereon, as shown in FIG. 12. The grooves 5 are formed with a defined depth and width, such as 6 mm by 3 mm, and separated by a defined distance, such as 5 cm.

Figure 9:
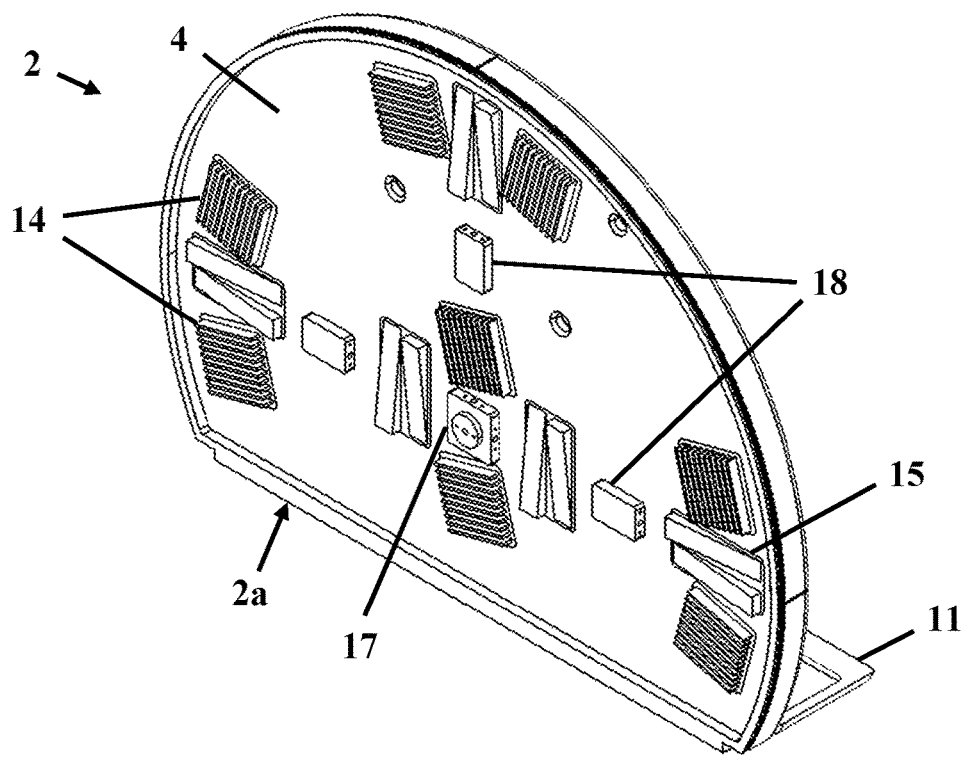
FIG. 9 is a perspective cutaway view of the vertical body of the phantom, with the front face removed to show internal features of the phantom.
Figure 10:
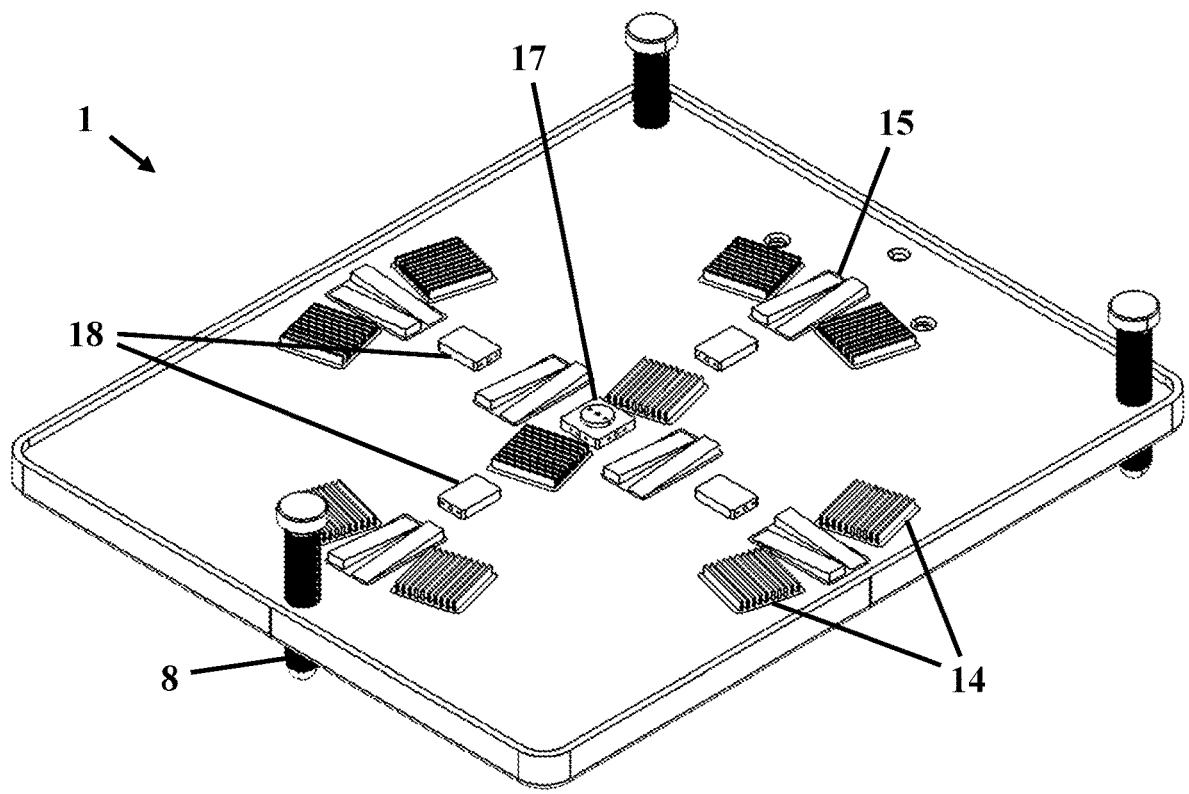
FIG. 10 is a perspective cutaway view of the base of the phantom, with the top of the base removed to show internal features of the phantom.
Figure 11:
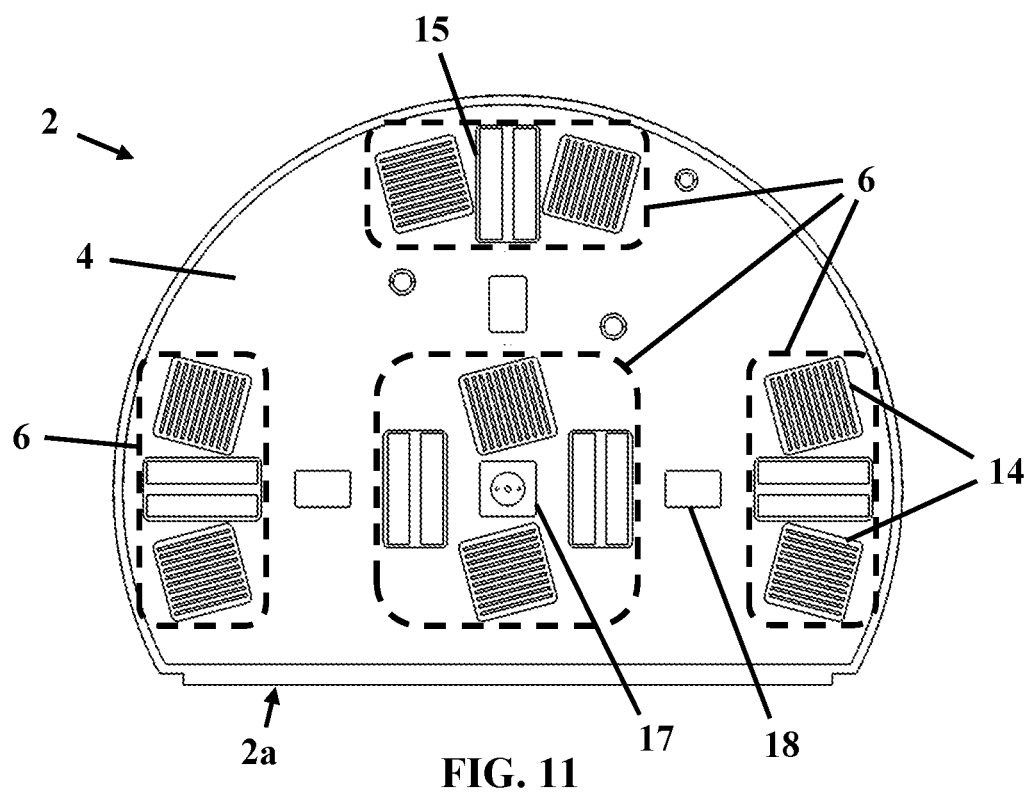
FIG. 11 is a front cutaway view of the vertical body of the phantom, as shown in FIG. 9.

Preferably, the interior face of the other opposing sheet 4 is generally flat with defined patterns of structures formed in one or more image quality zones 6 thereon that facilitate MRI image quality testing, as shown in FIGS. 9-11. As a result, when each sealed reservoir 3 is filled with MRI contrast media, one side of the reservoir 3 produces a grid pattern, which may be used to quickly visualize and quantify geometric distortion, while the other side of the reservoir 3 produces defined patterns in one or more image quality zones 6, which may be used to test MRI image quality.

Figure 14:
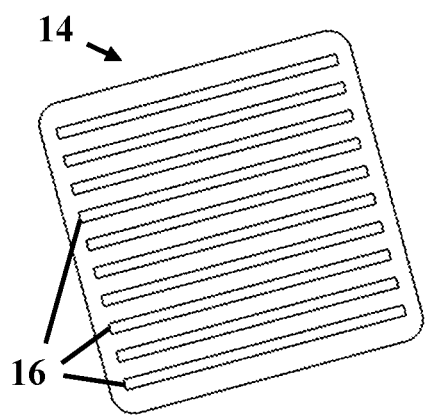
FIG. 14 is a front detail view of a modulation transfer function resolution structure of the phantom.
Figure 15:
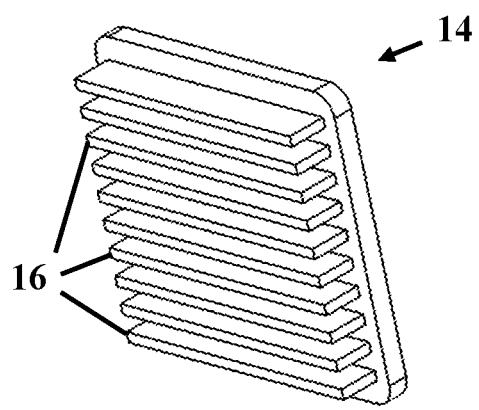
FIG. 15 is a perspective detail view of the modulation transfer function resolution structure, shown in FIG. 14.
Figure 18:
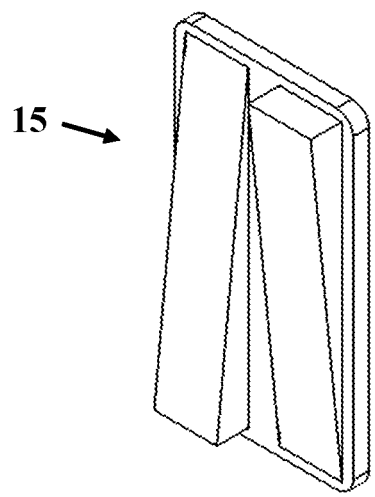
FIG. 18 is a perspective detail view of a slice thickness ramp of the phantom.

Preferably, the image quality zones 6 include modulation transfer function (MTF) resolution structures 14, as shown in FIGS. 14 and 15, and slice thickness ramps 15, as shown in FIG. 18. The MTF resolution structures 14 are based on IEC Standard 64-1 and have a series of parallel vanes 16 which define a plurality of line pairs that are detected by the imaging system. The MTF resolution structures 14 are offset from the measurement axis by 10°-15° and, preferably each image quality zone 6 has two MTF resolution structures 14. As shown in FIG. 11, each MTF resolution structures (per image quality zone 6) is offset from a different measurement axis. This permits both measurement axis to be tested in a single scan, eliminating the need to conduct one scan for the first axis, reposition the phantom, then conduct a second scan in order to test the second measurement axis.

Preferable one or two slice thickness ramps 15 are also provided in each image quality zone 6. As shown in FIG. 18, each of the slice thickness ramps 15 has two adjacent wedge-shaped structures, parallel to one another and facing in opposite directions. When imaged, more or less of the wedges appear, depending of the slice thickness of the image. The image can be compared with the known dimensions of the slice thickness ramps 15 to determine whether slice thickness of the image is properly calibrated.

Because the measurement of both MTF resolution structures 14 and slice thickness ramps 15 depend on gradient linearity, the image quality zones 6 are positioned at isocentre, but also near the outside edge of the phantom, so as to provide measurements away from the centre of the field of view of the imaging system. Since gradient linearity drops away with distance from the isocentre, it is useful to position structures for image quality measurement both at and off-isocentre.

The most common resolutions for MRI scanning are 1 mm, 1.5 mm, 2 mm, or 3 mm. Quick scans are normally conducted with a resolution of 3 mm. For this reason, the plane in which the grid is formed is preferably spaced apart from the isocentre of the phantom by a distance that is an integer multiple of 6 mm. This spacing of the grid, from the isocentre of the phantom, ensures that the grid will be centred within at least one slice of the image, regardless of whether the scan is made at 1 mm, 1.5 mm, 2 mm, or 3 mm resolution. The defined structures in the image quality zones 6 of the phantom are also preferably 6 mm thick. Additionally, any accessories attached to the attachment points 13 on the vertical body 2 are preferably mounted such that the centre of their imaging feature of interest is positioned at distance from the plane of the vertical body 2 of an integer multiple of 6 mm from the isocentre point of the phantom. With this configuration, at least one slice of the image will be centred around each image quality feature of the phantom, in the correct plane and orientation. As a result, technicians conducting quality assurance testing, either daily or less frequently, can minimize the number of scans required to complete the mandatory routine image quality testing. Some preferred embodiments of the present invention permit all of the regular daily image quality assurance testing for an MRI imaging system to be completed in a single scan.

Figure 4:
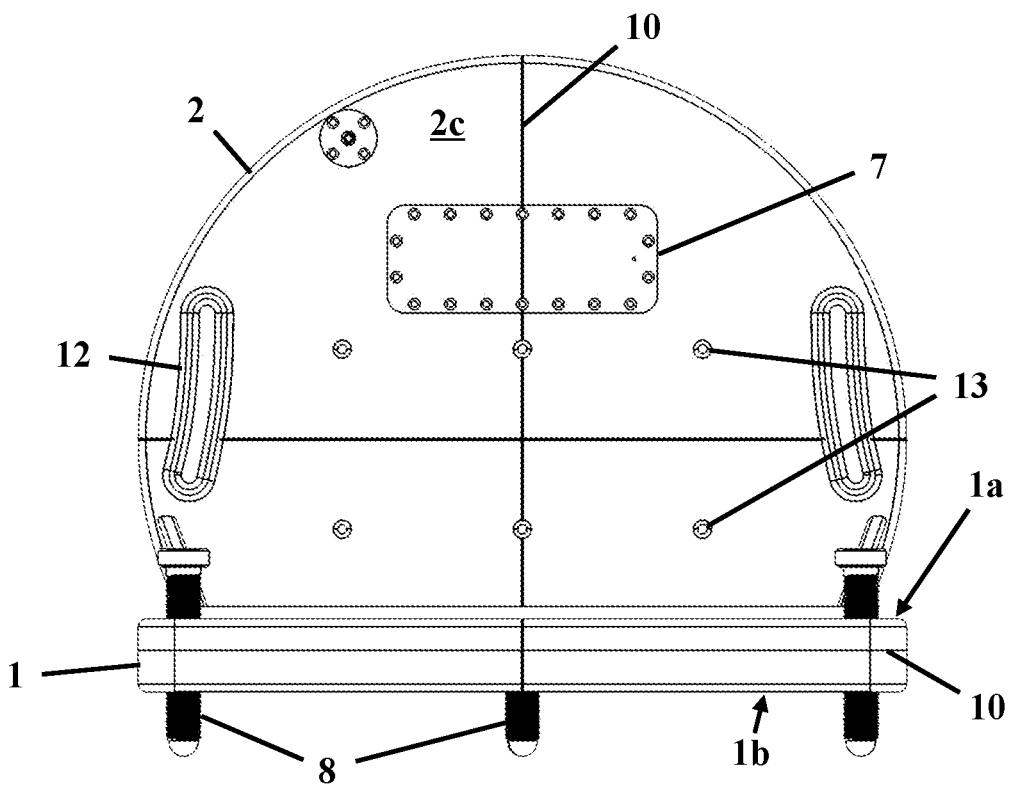
FIG. 4 is a rear view of the phantom.
Figure 5:
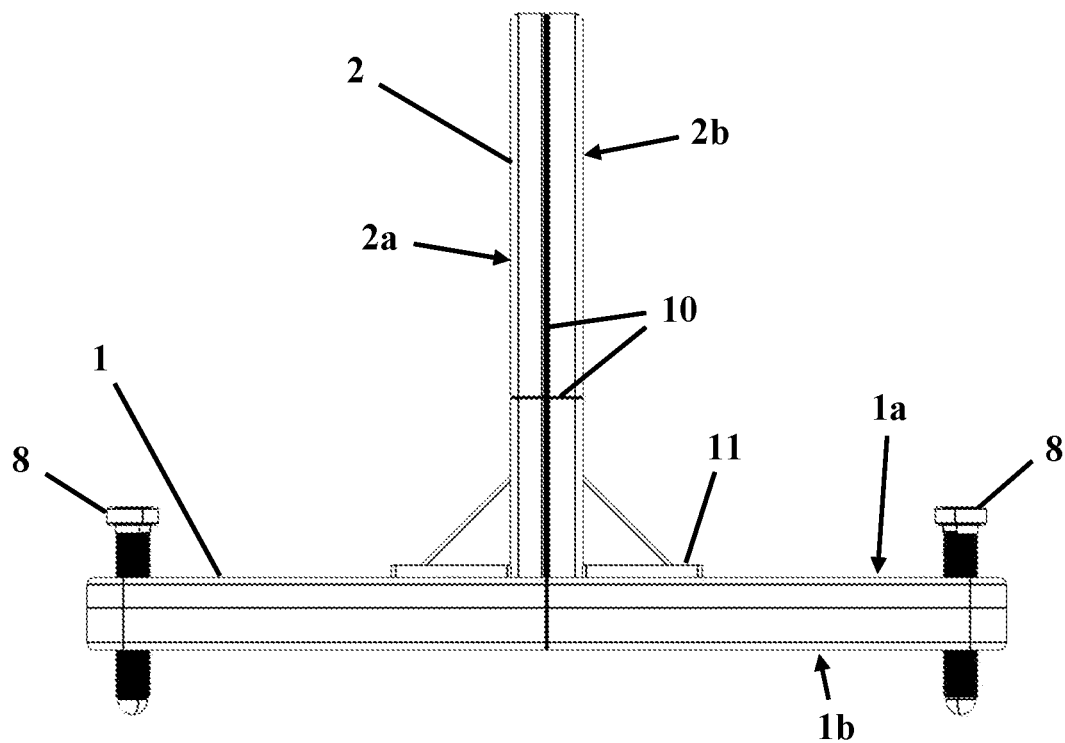
FIG. 5 is a side view of the phantom.
Figure 6:
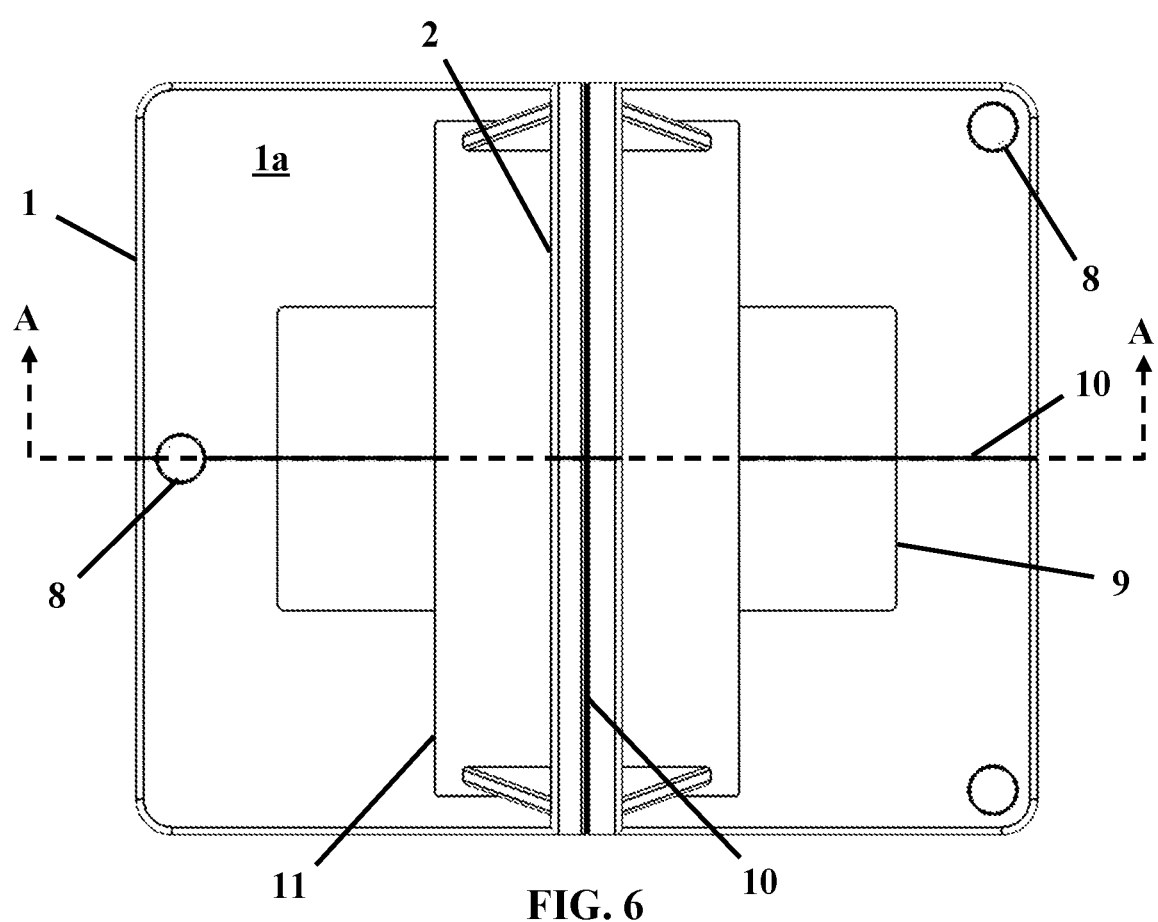
FIG. 6 is a top view of the phantom.
Figure 7:
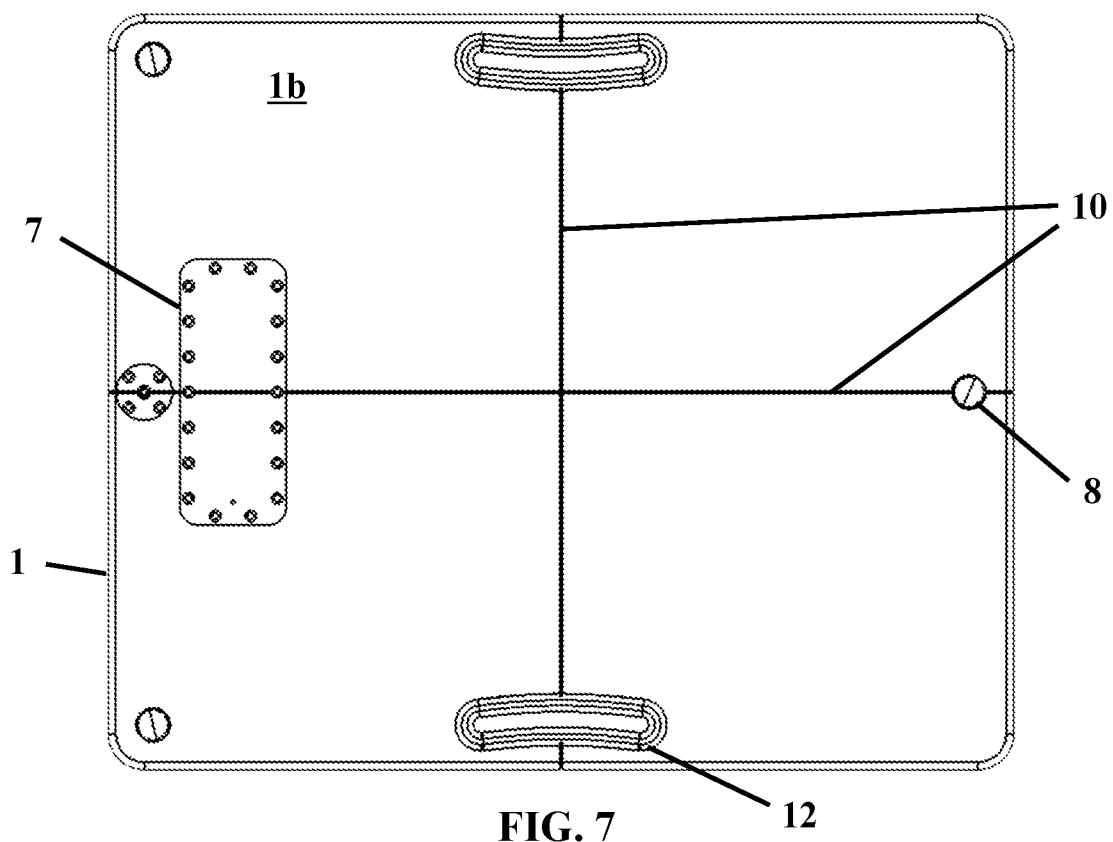
FIG. 7 is a bottom view of the phantom.

Optionally, as shown in FIGS. 4 and 7, either or both of the sealed reservoirs 3 may be configured with a first volume portion and a second variable volume portion or an expandable bladder 7 in fluid communication with the first volume portion. The second variable volume portion varies in response to changes in volume of the MRI contrast medium, to compensate for variations in temperature and pressure. Any accessories attached to the phantom, as described below, that also include one or more sealed reservoirs 3 may also be configured with a variable volume portion or an expandable bladder 7. Preferably, the temperature and pressure compensation is provided as described in U.S. Pat. No. 10,180,484 B2 or United States patent application publication number US 2019/0113591 A1, both in the name of the present applicant.

Figure 8:
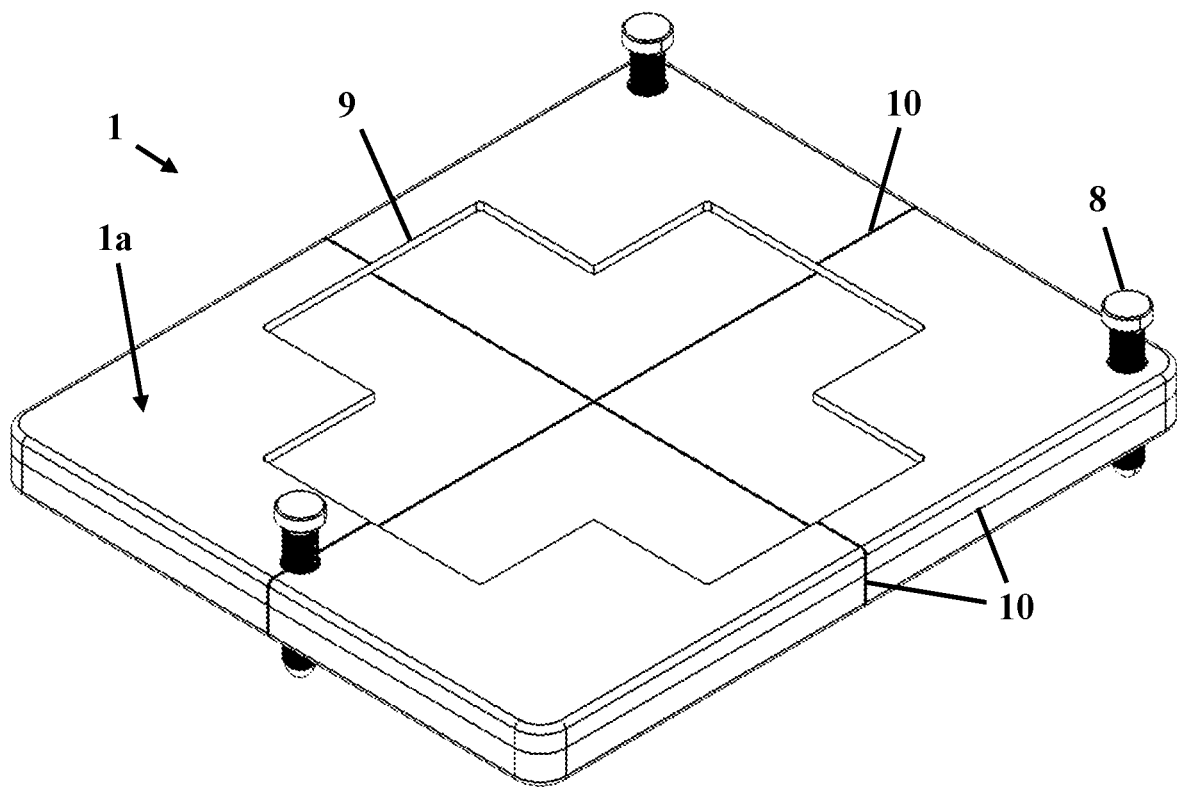
FIG. 8 is a perspective view of the base of the phantom.

The base 1 is generally rectangular and has adjustable supports 8 to permit leveling and height adjustment. A level indicator is provided to ensure the base 1 is level. The adjustable supports 8 permit the phantom to be positioned, for example, at the isocentre of the system to be tested, or at any other desired height. In certain circumstances, it may be desirable for the scan may be run on the base 1 alone, in which case the vertical body 2 may be removed, as shown in FIG. 8, and the base 1 may be raised to the isocentre of the system.

The top 1a of the base 1 is configured to engage with and support the vertical body 2 thereon. For example, the top 1a of the base 1 may have a recess 9 formed thereon in which the vertical body 2 is seated, as shown in FIGS. 1, 2, 8, and 13. Preferably, the recess is X-shaped, to permit the vertical body 2 to be positioned in the axial or sagittal plane. Where an expandable bladder 7 is provided on the base, it is positioned on the bottom 1b of the base 1, as shown in FIG. 7, to avoid any potential interference with the mounting of the vertical body 2.

The top 1a of the base 1 also has laser landmark targets 10 for positioning of the phantom and to enable testing and calibration of a laser bridge or other positioning apparatus associated with the system. Preferably, the laser landmark targets 10 are white lines within 1 mm wide grooves extending between the mid-point of each opposing side of the base 1 and continuing down the side edges. The laser landmark targets 10 provide a precise visual indication of any misalignment or twist of the phantom when placed on the patient table and facilitates precise alignment of the phantom with the laser alignment system. Any misalignment or twist apparent in imaging scans indicates improper calibration of the laser alignment system and/or patient table misalignments or twists in any of the six degrees of freedom (i.e. left-right, anterior-posterior, superior-inferior, roll, pitch, or yaw). Appropriate action can then be taken to correct any improper calibration, misalignment, or twist.

As shown in FIGS. 1-6, the vertical body 2 is generally circular with a flattened bottom 2a to facilitate mounting the vertical body 2 on the base 1. Preferably, the flattened bottom 2a of the vertical body 2 has flanges 11 that extend outwardly from the front and rear faces 2b and 2c to provide additional stability. In order to facilitate testing over a wide field of view, the vertical body 2, has a diameter of at least 35 cm, preferably 40 cm, although smaller sizes are possible. As shown in FIGS. 9 and 11-13, the underside of the vertical body 2 may be shaped to engage with the recess 9 on the top 1a of the base 1, in one or more positions, such as in the axial and sagittal planes, as described above.

The vertical body 2 has handles 12, or grips, to facilitate setup and repositioning of the vertical body 2 on the base 1. Preferably, the handles 12 are recessed into the front and rear faces 2b and 2c of the vertical body 2, so as not to interfere with the laser, during positioning or calibration of the laser positioning system. As shown in FIG. 7, the base 1 may also have handles 12 recessed into the bottom 1b of the base 1 adjacent the edge to facilitate handling of the base 1.

Figure 2:
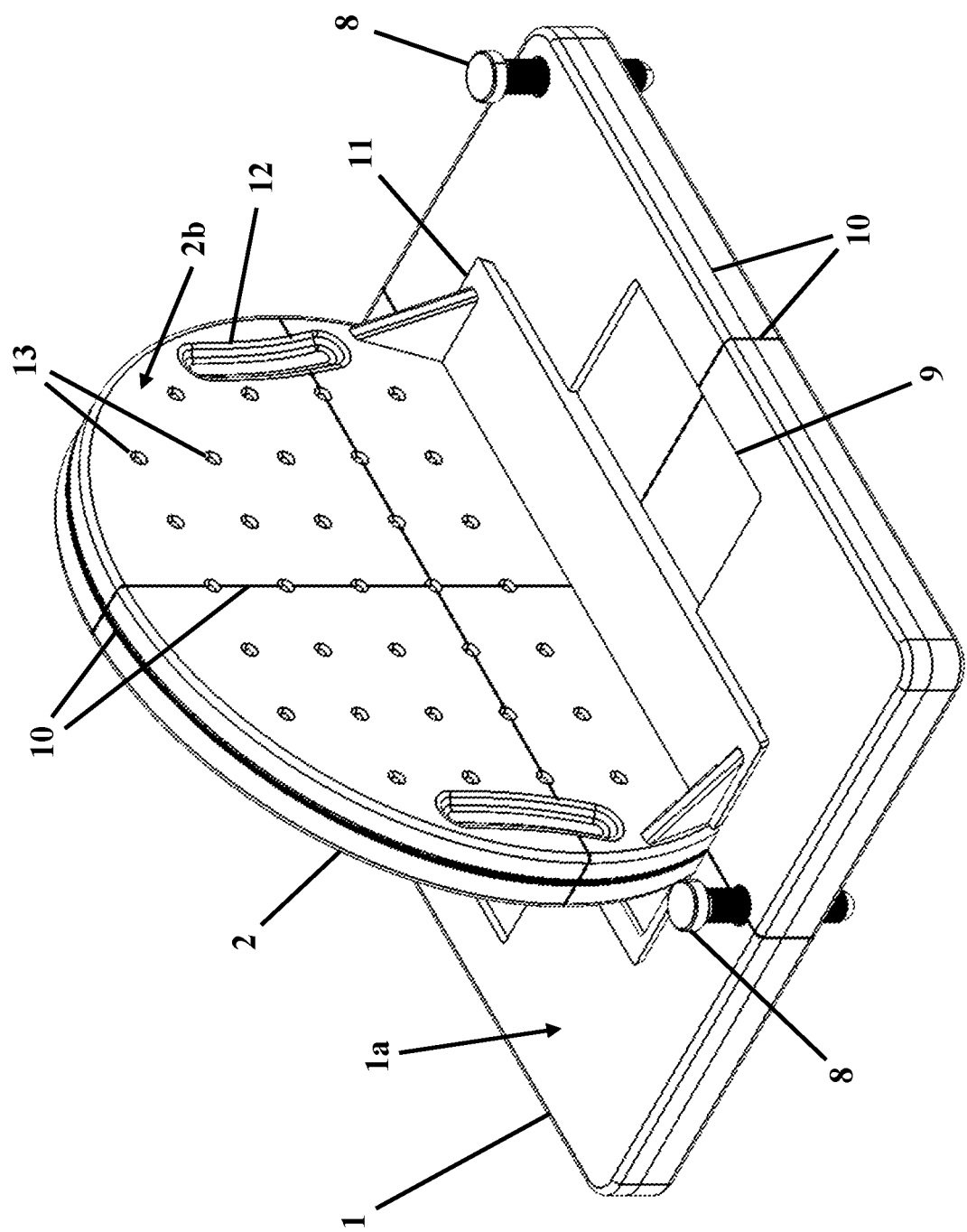
FIG. 2 is a perspective view of the phantom, with the vertical body rotated 90° on the base.
Figure 3:
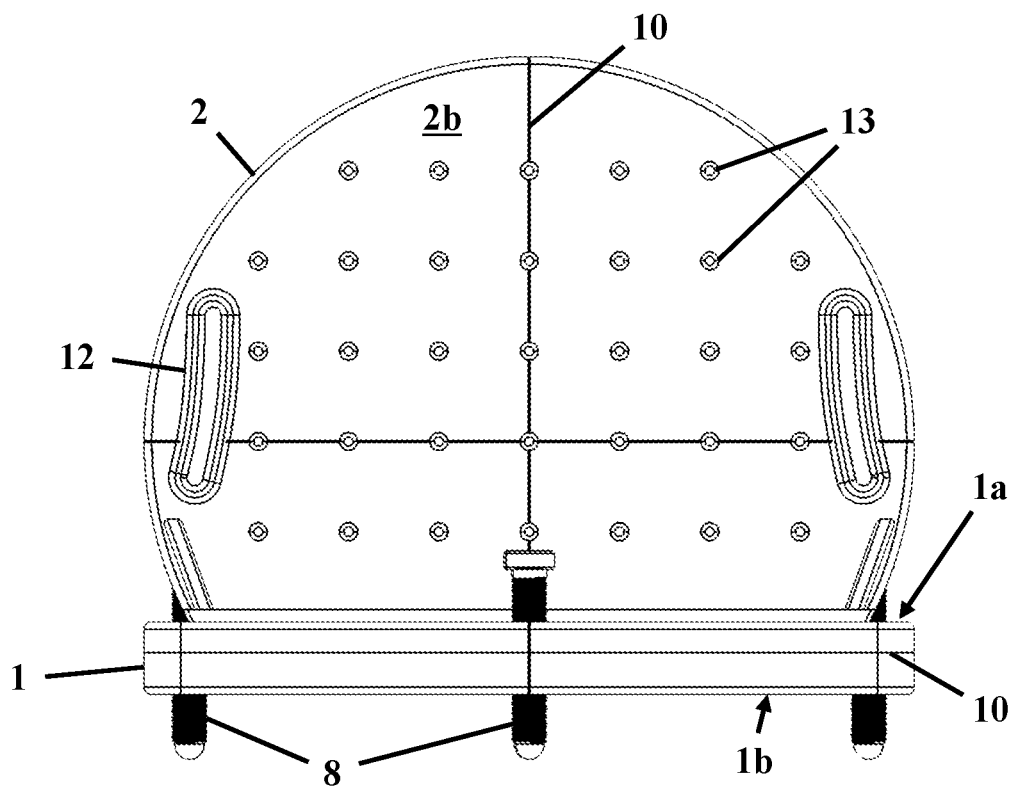
FIG. 3 is a front view of the phantom.

The vertical body 2 also has laser landmark targets 10, similar to those on the base 1. As shown in FIGS. 1-3, the front 2b of the vertical body 2 has a vertical line and a horizontal line crossing at the centre of the front 2b of the vertical body 2 and continuing across the perimeter edge. As shown in FIG. 4, the laser landmark targets 10 may also be similarly positioned on the rear 2c of the vertical body 2. As shown in FIGS. 1, 2, 5, and 6, the vertical body 2 also has a laser landmark target 10 on its perimeter edge, positioned in the plane of the reservoir 3. This laser landmark target 10 is preferably a white line within a 1 mm wide groove that is itself positioned within a 3 mm wide groove to improve visibility.

As shown in FIGS. 1-3, the front face 2b of the vertical body 2 is provided with a plurality of attachment points 13 for mounting a variety of accessories on the phantom to extend the testing capabilities of the phantom. The attachment points 13 are preferably threaded recesses to permit attachment of accessories by way of screw fasteners to the front face 2b of the vertical body 2. Optionally, the rear face 2c of the vertical body 2 may be provided with a plurality of attachment points 13 in addition to or instead of the front face 2b. The attachment points 13 are positioned at defined positions, such as at each of the intersecting points on the grid. The accessories may thereby be attached at known positions, such as at isocentre or defined distances above, below, or to either side of isocentre. As described above, these positions are preferably all integer multiples of 6 mm, so as to centre at least one image slice around the imaging feature of interest on the accessory, regardless of scan resolution.

Nearly any type of imaging or dosimetry target or detector may be attached to the phantom and used as an accessory. For example, suitable accessories may include: MR laser offset registration targets, multi-modality imaging targets, ion chamber holders, film cassettes, diode detectors, OSLD or TLD dosimetry detectors, and 3D gel dosimetry detectors. A "multi-modality imaging target" may be any target capable of measurement in more than two imaging modalities, such as MR, MV, CT, and PET. Many other MR-compatible imaging or dosimetry tools may be used as an accessory attached to the phantom, in order to facilitate additional desired measurements or functionality.

Preferably, the accessories are mounted on an attachment platform that may be attached against the front face 2b of the vertical body 2 to the attachment points 13. The platform has two apertures that are spaced apart so as to align with two attachment points on the front face 2b. The accessory may be positioned against the front face 2b at the desired position and attached by way of two screw fasteners. Optionally, plates or spacers may be used having defined thicknesses to provide a known offset from the front face 2b of the vertical body 2. Certain accessories may also be provided with laser landmark targets to facilitate precise positioning of the accessory in the system for testing.

By way of example, a multi-modality imaging target may be used as an accessory and attached to the front face of the vertical body 2. A preferred multi-modality imaging target is a hollow sphere made of acrylic having a sealed reservoir therein, filled with mineral oil, and a ceramic bead positioned inside the sealed reservoir. This type of multi-modality imaging target may be used to test a variety of imaging modalities, such as MR, MV, and CT.

Another exemplary accessory for use with the phantom is an ion chamber holder, which may be used to measure radiation dose. The ion chamber holder has a housing made of acrylic that contains a spherical tumour target within a mineral oil-filled sealed reservoir.

Another exemplary accessory is a film cassette 16, which may be used to provide additional data on radiation dose, beyond that available from testing with an ion chamber. Preferably, the film cassette has a slot for receiving a film cartridge and a sealed reservoir, filled with mineral oil, above and below the slot. Given the additional processing time required to develop the radio-sensitive film sheet, a film cassette may not be desirable for daily QA testing, but may be suitable for weekly or monthly testing. The film cassette accessory could be attached to the vertical body 2, in place of an ion chamber holder, for less frequent testing and then replaced with the ion chamber holder, for daily QA testing.

Figure 16:
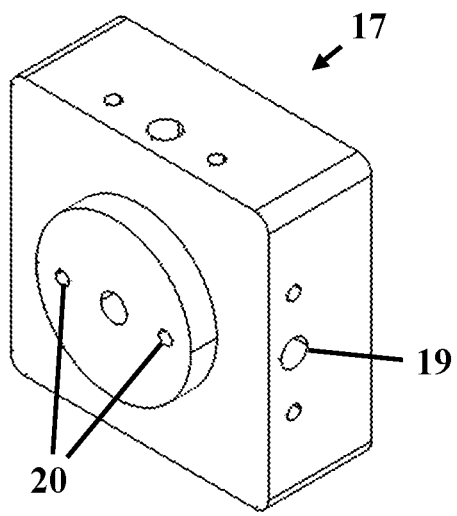
FIG. 16 is a perspective detail view of an isocentre indicator of the phantom.

Optionally, in addition to the laser landmark targets 10 to detect misalignment optically, the phantom may be configured to permit imaging twist detection. As shown in FIGS. 9 and 11, the vertical body 2 has an isocentre indicator 17 and three twist indicators 18 positioned in the same plane within the sealed reservoir 3. The isocentre indicator 17 and twist indicators 18 may also provide additional stability to the vertical body 2 and minimize any flexing of the opposing sheets when pressed. The imaging twist detection is described with reference to the vertical body 2, but could also or instead be provided on the base 1 in a similar fashion, as shown in FIG. 10. As shown in FIG. 16, the isocentre indicator 17 is a generally square block of acrylic with three orthogonal apertures 19 that cross in the centre and extend between the midpoints of the four opposing side edges. The apertures 19 in the isocentre indicator 17 are preferably 3 mm in diameter and permit a signal to be detected through the apertures.

Figure 17:
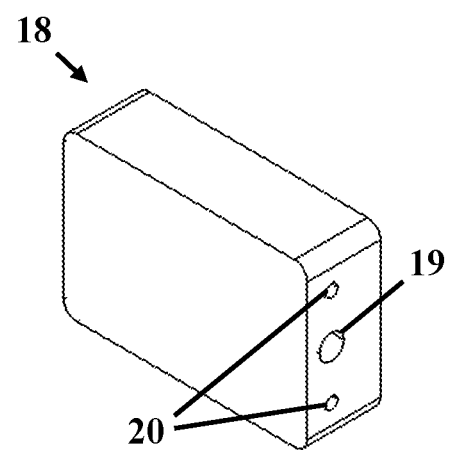
FIG. 17 is a perspective detail view of a twist indicator of the phantom.

As shown in FIG. 17, the four twist indicators 18 are generally rectangular blocks of acrylic and are positioned above, below, and to each side of the isocentre indicator 17 within the sealed reservoir 3. Each of the twist indicators 18 has an aperture 19 extending lengthwise through the centre of the twist indicator 18 that is precisely aligned (i.e. co-linear) with one of the apertures 19 through the isocentre indicator 17 and with the corresponding aperture 19 of the twist indicator 18 above, below, or on the opposite side of the isocentre indicator 17. Accordingly, two of the three apertures 19 through the isocentre indicator 17 and the apertures 19 through the twist indicators 18 are all aligned in the same plane. These apertures 19 are the same size, preferably 3 mm in diameter, as the apertures 19 in the isocentre indicator 17.

During imaging testing, a signal will pass through the apertures 19 and be detectable by the system. As a result, any twist, angle, or bend in the imaging alignment will result in a change or loss in the signal detected through the apertures and alert the operator of a problem with the imaging system. Optionally, the isocentre and twist indicators 17 and 18 may also have one or more smaller apertures 20, positioned and aligned in a similar way with one another, to permit detection of smaller twists, angles, or bends in the imaging alignment. Preferably, for the twist indicators 18, two parallel 1.5 mm diameter apertures 20 are positioned adjacent each of the 3 mm diameter apertures 19 and in the same plane as the 3 mm diameter apertures. For the isocentre indicator 18, four parallel 1.5 mm diameter apertures 20 are positioned adjacent to each of the 3 mm apertures 19 to provide twist detection in two orthogonal planes for each aperture 19. Two of the 1.5 mm diameter apertures 20 are positioned in the same plane as the 3 mm diameter apertures 19 and two are positioned in a second plane perpendicular to the first plane.

The phantom may be used by an operator to manually perform daily QA testing on a variety of imaging systems by conducting a variety of pre-determined scans and manually analyzing the results to ensure the system is performing within the specified operating parameters. Alternatively, software may be used to automate some or all of the scanning and data analysis tasks and to prepare daily QA reports. Using software for automated data analysis in imaging QA has been shown to reduce inter and intra-observer variability, leading to more uniform testing and calibration.

The present invention has been described and illustrated with reference to an exemplary embodiment, however, it will be understood by those skilled in the art that various changes may be made and equivalents may be substituted for elements thereof without departing from the scope of the invention as set out in the following claims. Therefore, it is intended that the invention not be limited to the particular embodiments disclosed herein.

What is claimed is:

1. A MRI quality assurance phantom, comprising a base and a vertical body mounted on the base, the vertical body having a housing made of a MRI invisible material and enclosing a sealed reservoir filed with a MRI signal producing material, wherein the vertical body has a generally planar external face with a plurality of attachment points thereon for attachment of one or more accessories to the exterior of the face of the vertical body at one or more of a plurality of known positions relative to the vertical body, wherein the housing has parallel and generally planar interior walls defining a generally disc-shaped sealed reservoir with a diameter and a thickness less than the diameter and the interior walls having one or more defined structures formed thereon.

2. The MRI quality assurance phantom of claim 1, wherein the diameter of the sealed reservoir is at least about 35 cm and the thickness of the sealed reservoir is up to about 6 mm.

3. The MRI quality assurance phantom of claim 2, wherein the diameter of the sealed reservoir is about 40 cm and the thickness of the sealed reservoir is up to about 6 mm.

4. The MRI quality assurance phantom of claim 3, wherein the one or more defined structures comprises a plurality of grooves defining a grid.

5. The MRI quality assurance phantom of claim 1, wherein the one or more defined structures comprises a plurality of defined structures located within a plurality of image quality zones spaced apart within the plane of the sealed reservoir.

6. The MRI quality assurance phantom of claim 5, wherein a first image quality zone is located centrally within the sealed reservoir and a second image quality zone is spaced apart from the first image quality zone in the plane of the sealed reservoir.

7. The MRI quality assurance phantom of claim 1, wherein one or both of the base and the vertical body have laser landmark targets to facilitate visual alignment using a laser alignment system.

8. The MRI quality assurance phantom of claim 1, wherein one or both of the base and the vertical body have integrated handles recessed therein.

9. The MRI quality assurance phantom of claim 1, wherein the base has adjustable feet to permit height adjustment.

10. The MRI quality assurance phantom of claim 1, wherein the MRI signal producing material is a MRI contrast medium.

11. The MRI quality assurance phantom of claim 10, wherein the MRI contrast medium is a mineral oil with a close susceptibility match to human tissue and the MRI invisible material is acrylic.

12. The MRI quality assurance phantom of claim 1, wherein the sealed reservoir comprises a first volume portion and a second variable volume portion in fluid communication therewith, wherein the second variable volume portion varies in response to changes in the volume of the MRI signal producing material.

13. A MRI quality assurance phantom, comprising a base and a vertical body mounted on the base, the vertical body having a housing made of a MRI invisible material and enclosing a sealed reservoir filed with a MRI signal producing material, wherein the vertical body has a generally planar face,
wherein the housing has parallel and generally planar interior walls defining a generally disc-shaped sealed reservoir with a diameter and a thickness less than the diameter and the interior walls having one or more defined structures formed thereon,
wherein the one or more defined structures comprises a plurality of defined structures located within a plurality of image quality zones spaced apart within the plane of the sealed reservoir, and
wherein each image quality zone contains a plurality of defined structures, comprising modulation transfer function resolution structures and slice thickness ramps.

14. The MRI quality assurance phantom of claim 13, wherein at least one modulation transfer function resolution structure is configured to measure a first measurement axis and at least one modulation transfer function resolution structure is configured to measure a second measurement axis.

15. A MRI quality assurance phantom, comprising a base and a vertical body mounted on the base, the vertical body having a housing made of a MRI invisible material and enclosing a sealed reservoir filed with a MRI signal producing material, wherein the vertical body has a generally planar face,
wherein the housing has parallel and generally planar interior walls defining a generally disc-shaped sealed reservoir with a diameter and a thickness less than the diameter and the interior walls having one or more defined structures formed thereon,
wherein the base has a housing made of a MRI invisible material and enclose a sealed reservoir filed with a MRI signal producing material, and
wherein the base has a generally planar top surface having an X-shaped recess thereon.

16. The MRI quality assurance phantom of claim 15, wherein the vertical body is generally circular with a flattened bottom shaped to fit in the X-shaped recess on the base.

17. The MRI quality assurance phantom of claim 16, wherein the diameter of the sealed reservoir in the vertical body is at least 35 cm and the thickness of the sealed reservoir in the vertical body is about 6 mm.

18. The MRI quality assurance phantom of claim 16, wherein the diameter of the sealed reservoir in the vertical body is 40 cm and the thickness of the sealed reservoir in the vertical body is about 6 mm.

19. The MRI quality assurance phantom of claim 15, having an isocentre indicator, comprising a generally square block of MRI invisible material having three orthogonal apertures therethrough positioned within the sealed reservoir.

20. The MRI quality assurance phantom of claim 19, having one or more twist indicators, each comprising a generally rectangular block of MRI invisible material having an aperture extending therethrough positioned within the sealed reservoir and aligned with the isocentre indicator, so as to align the aperture through the twist indicator with one of the orthogonal apertures through the isocentre indicator.

21. The MRI quality assurance phantom of claim 19, wherein the generally planar face of the vertical body has a plurality of attachment points thereon for attachment of one or more accessories to the face of the vertical body at one or more of a plurality of known positions relative to the vertical body, wherein the one or more accessories have an image quality feature of interest positioned at a distance from the vertical body of an integer multiple of 6 mm from the isocentre indicator.

22. The MRI quality assurance phantom of claim 21, wherein the one or more accessories are selected from the group consisting of: MR laser offset registration targets, multi-modality imaging targets, ion chamber holders, film cassettes, diode detectors, OSLD or TLD dosimetry detectors, and 3D gel dosimetry detectors.

\* \* \* \* \*